United States Patent
Liu et al.

(10) Patent No.: US 8,658,401 B2
(45) Date of Patent: Feb. 25, 2014

(54) METHOD FOR PREPARING HIGH PURITY L-α GLYCERYLPHOSPHORYLCHOLINE

(75) Inventors: Yuanfa Liu, Wuxi (CN); Kangyi Zhang, Wuxi (CN); Xingguo Wang, Wuxi (CN); Xiangyun Qian, Wuxi (CN); Li Zhou, Wuxi (CN); Zhihua Song, Wuxi (CN)

(73) Assignee: Jiannan University, Wuxi, JS (CN)

( * ) Notice: Subject to any disclaimer, the term of this patent is extended or adjusted under 35 U.S.C. 154(b) by 244 days.

(21) Appl. No.: 13/071,126

(22) Filed: Mar. 24, 2011

(65) Prior Publication Data

US 2012/0244583 A1    Sep. 27, 2012

(51) Int. Cl.
*C12P 9/00*    (2006.01)

(52) U.S. Cl.
CPC ........................... *C12P 9/00* (2013.01)
USPC ............ 435/131; 435/132; 435/159; 435/155; 435/41

(58) Field of Classification Search
None
See application file for complete search history.

(56) References Cited

U.S. PATENT DOCUMENTS

| | | | |
|---|---|---|---|
| 4,607,011 A * | 8/1986 | Kaplan et al. | 435/131 |
| 5,250,719 A * | 10/1993 | Tronconi | 558/146 |
| 5,538,874 A * | 7/1996 | Hattori et al. | 435/128 |
| 7,189,544 B2 * | 3/2007 | Schmitt et al. | 435/134 |
| 2011/0312006 A1 * | 12/2011 | Valentin et al. | 435/18 |
| 2012/0100580 A1 * | 4/2012 | Tanaka et al. | 435/128 |

FOREIGN PATENT DOCUMENTS

| KR | 1997-0043059 | * | 7/1997 |
|---|---|---|---|
| WO | WO 03091263 A1 | * | 11/2003 |

OTHER PUBLICATIONS

Salituro et al., "Isolation by Low-Pressure Column Chromatography", Methods in Biotechnology: Natural Products Isolation, vol. 4, pp. 111-140, 1998.*
Ichihara et al., "Synthesis of phosphatidylcholine: An improved method without using the cadmium chloride complex of sn-glycero-3-phosphocholine", Chemistry and Physics of Lipids, vol. 137, pp. 94-99, 2005.*

* cited by examiner

*Primary Examiner* — Rebecca Prouty
*Assistant Examiner* — Richard Ekstrom
(74) *Attorney, Agent, or Firm* — Lili Chen

(57) ABSTRACT

Disclosed is a method for preparing L-α-Glycerylphosphorylcholine with high yields and purity. The method uses phospholipase $A_1$-based enzymatic hydrolysis, ion-exchange resin purification and silica gel column chromatography to prepare L-α-glycerylphosphorylcholin with purity up to 99.8% and a final yield up to 78.4%. The method disclosed is simple, cost-effective, environmentally friendly, and adaptable to industrial applications.

14 Claims, 5 Drawing Sheets

_US 8,658,401 B2_

METHOD FOR PREPARING HIGH PURITY L-α GLYCERYLPHOSPHORYLCHOLINE

FIELD OF THE INVENTION

This invention relates to a method for the preparation of L-alpha glycerylphosphorylcholine. It especially relates to a method for the preparation of L-alpha glycerylphosphorylcholine using phospholipase $A_1$ hydrolysis and silica gel column chromatography.

BACKGROUND OF THE INVENTION

L-α-Glycerylphosphorylcholine (L-α-GPC) is a naturally existing water-soluble phospholipid, which is the precursor for making acetylcholine and phosphatidylcholine in the body.

L-α-GPC has important medical applications, for example, it can enhance cognitive ability and even repair the partial damaged cognitive ability in early Alzheimer's disease. Furthermore, it can protect liver tissues from poisonous carbon tetrachloride and fatty acid penetration caused by high lipoprotein diet. It can also enhance body's resistance to high blood fat and protect blood vessels.

Currently, major methods in domestic and international research for preparing L-α-GPC are chemical synthesis, chemical hydrolysis, chemical alcoholysis and enzymatic hydrolysis. Methods of purification include solvent extraction, precipitation, recrystallization, and resin column chromatography.

L-α-GPC was firstly purified from cattle pancreatic (GSchmidt, J. Biochem, 1945, 161, 523) using a solvent extraction method, which was limited by the availability of raw materials and put a limit on the manufacturing scale. With the advance of new technologies, methods of chemical synthesis, chemical hydrolysis, and chemical alcoholysis were developed for making L-α-GPC. Purification methods such as calcium precipitation, recrystallization and resin column chromatography were also developed. However, these methods pose different levels of difficulties in preparing L-α-GPC with high yields and optical purity at industrial manufacturing scale. Furthermore, the chemical methods bring great challenges to the environment. Enzymatic synthesis process brings innovative ways in preparing L-α-GPC, but how to obtain high yields and purity using enzymatic methods is still very challenging.

In 1954, Mcarthur et al (U.S. Pat. No. 2,864,848) disclosed a method for the preparation of L-α-GPC using mercuric chloride hydrolysis of lecithin and removing by-products by precipitation in the form of mercury salts. A disadvantage of this method is that the residual mercury ion and raw phosphatidylcholine can not be easily removed and needs further purification through calcium precipitation and resin column chromatography, which not only increases the complexity of the preparation process, but also reduces the final yield.

In order to eliminate metal ion residues and increase the purity of the product, Cailo Myriam Gozzoli and Scolastico (UK. Patent GB. 2,058,792 A) used resin column chromatography to prepare L-α-GPC. The method comprises of a series of processes, such as alcoholysis, solvent extraction, ion exchange resin, and activated carbon decolorization, which results in products with massive toxic residue and low optical purity.

As such, there is a great need in the art for technologies to prepare L-α-GPC with high yields and optical purity in a cost-effective and environmentally friendly way. The present invention satisfies this need and provides other benefits as well.

DETAILED DESCRIPTION OF THE INVENTION

Figure 1:
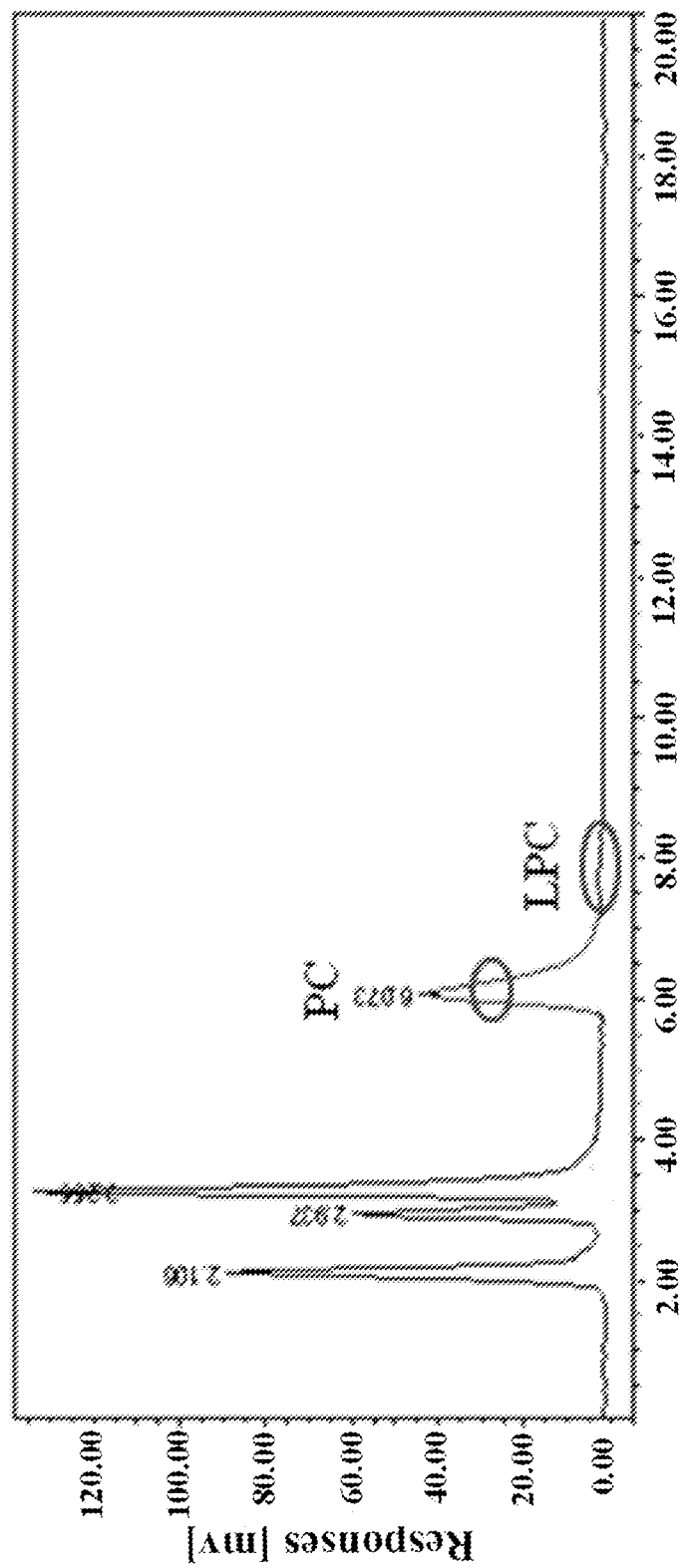
FIG. 1 shows the HPLC-ELSD analysis of phospholipids powder. Phospholipids powder is a mixture with phosphatidylcholine (PC), phosphatidylethanolamine (PE), phosphatidylinositol (PI), lysophosphatidylcholine (LPC), etc. The content of PC is about 20.3% and the retention time of PC is 6.073 minute.
Figure 2:
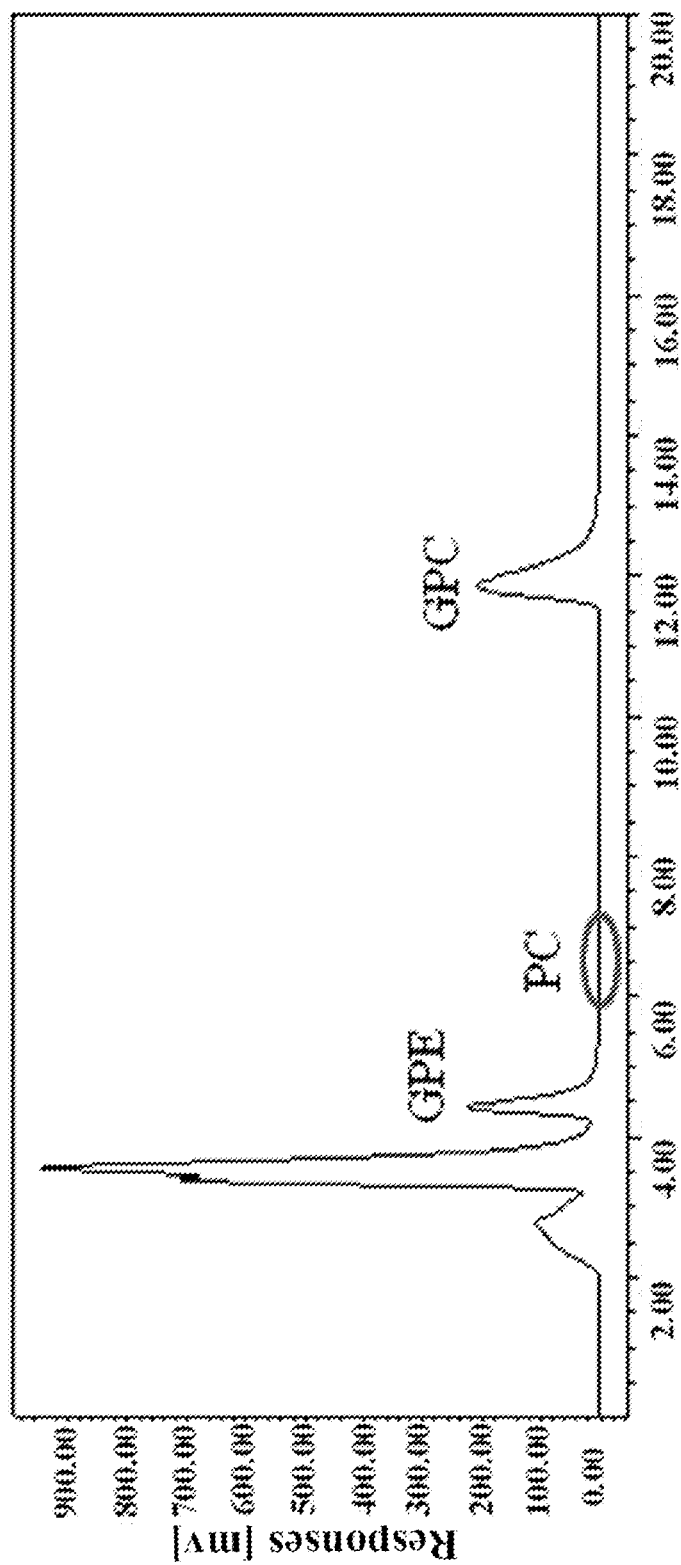
FIG. 2 shows the HPLC-ELSD analysis of phospholipids powder after phospholipase $A_1$ hydrolysis. There is almost no detectable PC in FIG. 2. The retention times of GPE (glycerophosphoethanolamine) and L-α-GPC are 4.517 min and 12.013 min, respectively.
Figure 3:
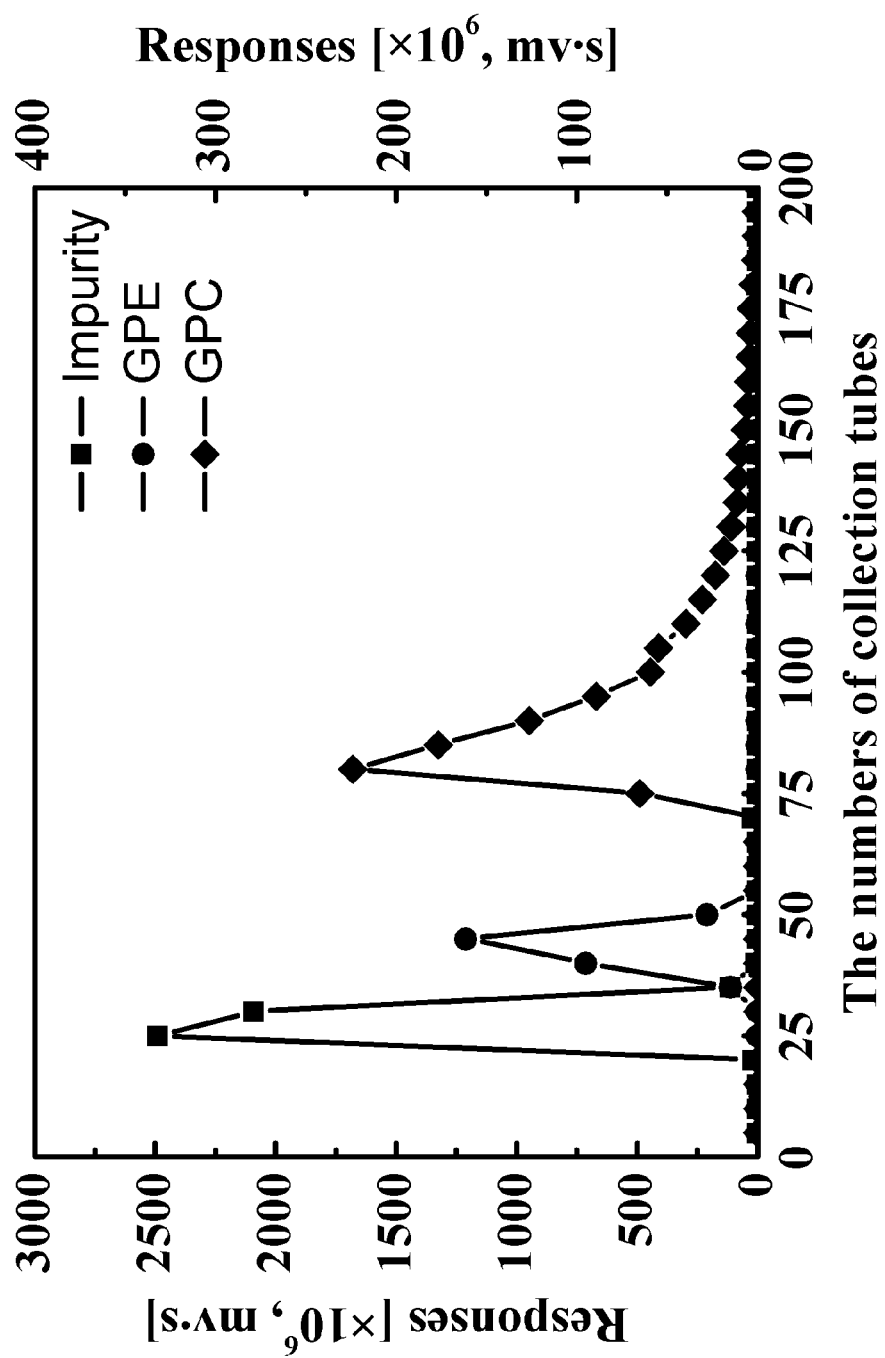
FIG. 3 shows the collection of L-α-GPC during silica gel column chromatography purification. It can be seen from FIG. 3 that L-α-GPC can be well separated from GPE and other by-products using silica gel column chromatography.
Figure 4:
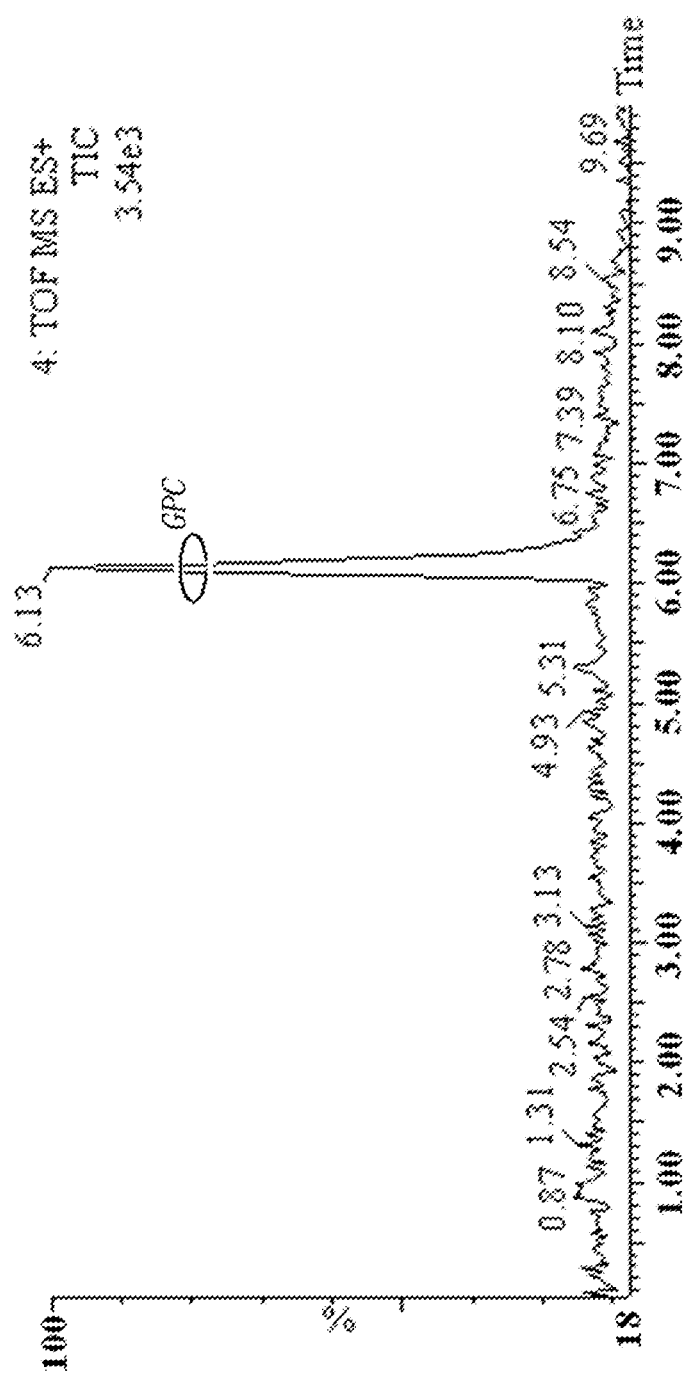
FIG. 4 shows the LC-MS analysis of obtained L-α-GPC. The purity of L-α-GPC is close to 100%.
Figure 5:
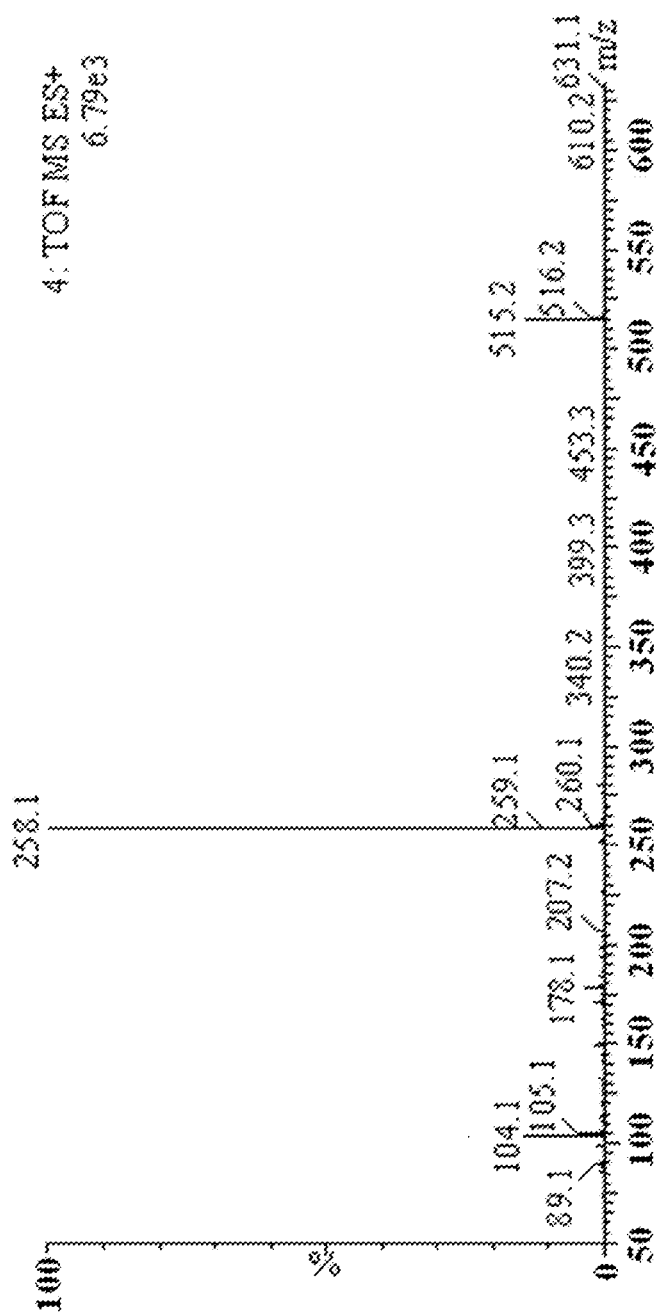
FIG. 5 shows the LC-MS analysis of obtained L-α-GPC. The corresponding mass to charge ratio of the peak at 5.8 min is 258, which confirms that the peak product is L-α-GPC with a molecular weight of 258.

The present invention provides a simple and cost-effective method for preparing L-α-GPC with high yields and purity, which can be easily adapted to industrial applications. The main feature of the present invention is to use the phospholipase $A_1$-based enzymatic hydrolysis for generation of L-α-GPC and the silica gel column chromatography for purification. The silica gel column chromatography purification is advantageous because it enables removal of the majority of by-products in one simple step. The enzymatic method of the invention can produce L-α-GPC with high chemical and optical purity without using harmful organic solvents, thus providing an effective and environmentally friendly method for the preparation of L-α-GPC.

The method of the present invention includes the following steps:

i, hydrolyze a phospholipid solution, which contains phosphatidylcholine, by phospholipase $A_1$ in the presence of calcium salts to generate Sn-2-lysophosphatidylcholine (Sn-2-LPC); the Sn-2 fatty acid of Sn-2-LPC moves to the Sn-1 position through spontaneous acyl migration to generate $S_n$-1-lysophosphatidylcholine (Sn-1-LPC); Sn-1-LPC is further hydrolyzed by phospholipase $A_1$ to generate a GPC mixture with L-α-GPC;

ii, use ion-exchange resins to eliminate the residual ions in the GPC mixture;

iii, use silica gel column chromatography to separate L-α-GPC from the GPC mixture.

More detailed information about each step is provided as following:

1, Enzymatic Hydrolysis:

Dissolve phospholipids (e.g. food-grade lecithin powder, alcohol-soluble phospholipids, and high purity phosphatidylcholine) which contain certain amounts of phosphatidylcholine in deionized water at a liquid-solid ratio of 1:10-1:30 g/mL; Stir the solution until well mixed. Add 2-10% (CaXn (g): phospholipids (g)) calcium salt ($CaX_n$) and mix well. Add 190 U-950 U phospholipase $A_1$ for each gram of the phospholipids and incubate the mixture with stirring at 30-60° C. for 3 to 6 hours until the enzyme hydrolysis reaction is complete. The reaction mixture is centrifuged to precipitate the insoluble materials. The soluble and insoluble materials are separated after centrifugation, resulting in a clear GPC mixture solution to be used in the next step.

2, Ion Exchange Resin Purification:

Use a cation-exchange resin to eliminate $Ca^{2+}$ and an anion-exchange resin to eliminate $Cl^-$. The cation-exchange resin can be, for example, a hydrogen form of a strong acid cation exchange resin, a weak acid cation exchange resin, or a macroporous type cation exchange resin. The anion exchange resin is a hydroxide form of a strong base anion exchange resin, a weak base anion exchange resin, or a macroporous type anion exchange resin.

3, Silica Gel Column Chromatography Purification.

Add silica gel to a low carbon chain alcohol and prepare a silica gel column according to common procedures known to those skilled in the art. The amount of silica gel is about 20 to 100 times of the weight of the GPC mixture. For example, 50 g of silica gel can be used to separate 1 g of sample (dry weight). The volume of fraction to be collected is about 1 to 10 mL for each gram of sample. For example, to separate two grams of samples, the collection will be performed at 20 mL/fraction. Elute with 0-100% low carbon chain alcohol (v:v, alcohol:water) at a flow rate of 0.5-4 mL/min. Eluted fractions are monitored by HPLC-ELSD and fractions of the same substance are combined. The low carbon chain alcohol used herein refers to methanol, ethanol, propanol, butanol, isobutanol, pentanol, hexanol, and isomers of pentanol and hexanol.

4, Decoloring.

The L-α-GPC fraction is mixed with a decolorant such as activated carbon or attapulgite under heated conditions and filtered to obtain a pure and clear product of L-α-GPC.

The present invention provides a new method for preparing L-α-GPC using phospholipase $A_1$-based hydrolysis and silica gel column chromatography purification. The enzyme reaction is conducted in aqueous solution under mild conditions. No organic solvent is needed in the reaction. Under the optimized condition for enzyme reactions, the conversion rate of L-α-GPC is increased to 97%. Using silica gel column chromatography for purification, the chemical purity of the final product is 99.8% and the final yield of 78.4% can be obtained. The final product also has high optical purity of 99%. The silica gel can be regenerated and reused. The present invention provide a solution to several problems in the existing enzymatic methods such as low conversion rate, low purity, difficult and complicated purification process, high production cost, pollution to the environment. The method of the present invention is simple, cost-effective, environmentally friendly, and can be adaptable to a large-scale industrial production.

EXAMPLES

The invention is further illustrated by the following examples. It is to be understood that the examples are used only for illustration purposes, not to be used to limit the scope of the invention. The scope of the invention should only be construed based on the claims of the invention.

Example 1

Prepare L-α-GPC from Lecithin Powders

The raw material used in this example is a food-grade lecithin powder, which contains about 20.3% of phosphatidylcholine.

Add 50 g food-grade lecithin powder to a three-necked flask with 500 mL deionized water and stir at 300 r/min until homogeneously mixed. Add 2 g Calcium Chloride and 1 mL phospholipase $A_1$ (9500 U/mL, Novozymes A/S, Denmark) into the raw material solution, incubating at 35° C. for 3 hours. Remove the insoluble materials from the reaction mixture by centrifugation and vacuum filtration. Use strong acid cation exchange resins (001×7, exchange capacity of 1800 mmol/L) to remove $Ca^{2+}$, while use maeroporous acrylic weak acidic anion exchange resin (D311, exchange capacity of 2200 mmol/L) to remove $Cl^-$ in the GPC mixture. Rotation evaporate at 60° C. to dry the GPC mixture, and then dissolve the GPC mixture in methanol.

Using HPLC-ELSD analysis, 2.97 g L-α-GPC was obtained in the methanol solution above, and the corresponding yield is 90.1%. Dissolve 148.5 g silica gel in methanol and prepare silica gel column according to common procedure for the following separation; elute with 10% methanol solution (v:v, methanol:water) at the flow rate of 2 mL/min, collect the elute in 30 mL/fraction. Combine fractions with L-α-GPC after HPLC-ELSD analysis. The L-α-GPC fraction was decolorized with activated carbon at 90° C. for 1 hour, and dried under reduced pressure at 45° C. 2.33 g high purity L-α-GPC was obtained at the end with a final yield of 78.4%. The silica gel can be regenerated for more than 10 times at 120-150° C. for 3 hours.

The properties of L-α-GPC obtained from three examples are shown in Table 1.

TABLE 1

| | The properties of the obtained L-α-GPC | | | | | | |
|---|---|---|---|---|---|---|---|
| Example | output | yield | TLC | chemical purity | optical purity | mp | $[\alpha]_D^{20}$ |
| 1 | 2.33 g | 78.4% | small amount spots | 99.2% | 99% | 142-143° C. | −2.8° |
| 2 | 6.82 g | 76.1% | small amount spots | 98.8 | 99% | 142-143° C. | −2.5° |
| 3 | 9.46 g | 77.8% | small amount spots | 99.8% | 99% | 142-143° C. | −2.7° |

Example 2

Preparation of L-α-GPC from Alcohol-Soluble Phospholipids

The raw material used in this example was alcohol-soluble phospholipids, which contains about 60.2% of phosphatidylcholine.

Add 50 g phospholipids to a three-necked flask with 1000 mL deionized water and stir at 300 r/min until well mixed. Add 1 g Calcium Bromide and 3 mL phospholipase $A_1$ (9500 U/mL, Novozymes A/S, Denmark) into the raw material solution, incubating at 30° C. for 5 hour. Remove the insoluble materials from the reaction mixture by centrifugation and vacuum filtration. Use strong acid cation exchange resins (001×7, exchange capacity of 1800 mmol/L) to remove $Ca^{2+}$, while use maeroporous acrylic weak acidic anion exchange resin (exchange capacity of 2200 mmol/L) to remove $Cl^-$ in the GPC mixture. Rotation evaporate at 75° C. to dry the GPC mixture, and then dissolve the GPC mixture in ethanol.

Using HPLC-ELSD analysis, 8.96 g L-α-GPC was obtained from the ethanol solution prepared above with a corresponding yield of 89.1%. Add 268.1 g silica gel in ethanol and prepare a silica gel column according to a standard procedure; elute with 10% ethanol solution (v:v, ethanol:water) at the flow rate of 0.5 mL/min, collect the elute in 10 mL/fraction. Combine the L-α-GPC fractions after HPLC-ELSD analysis. The L-α-GPC fraction was decolorized with activated carbon at 90° C. for 1 hour and dried under reduced pressure 60° C. 6.82 g high purity L-α-GPC was obtained at the end with a final yield of 76.1%.

Example 3

Preparation of L-α-GPC from High Purity Phosphatidylcholine

The raw material used in this example is alcohol-soluble phospholipids purified by low temperature crystallization, which contains about 81.5% of phosphatidylcholine.

Add 50 g phospholipids to a three-necked flask with 1500 mL deionized water and stir at 300 r/min until well mixed. Add 5 g Calcium Iodide and 5 mL phospholipase $A_1$ (9500 U/mL, Novozymes A/S, Denmark) into the mixed solution and incubate at 60° C. for 6 hour. Remove the insoluble materials from the reaction mixture by centrifugation and vacuum filtration and a clear GPC mixture solution was obtained. Use strong acid cation exchange resins (001×7, exchange capacity of 1800 mmol/L) to remove $Ca^{2+}$, while use maeroporous acrylic weak acidic anion exchange resin (exchange capacity of 2200 mmol/L) to remove CF. Rotation evaporate at 45° C., and then dissolve the GPC in ethanol.

Using HPLC-ELSD analysis, 12.17 g L-α-GPC was obtained from the ethanol solution above, and the corresponding yield is 89.6%. Add 304.5 g silica gel in ethanol and prepare silica gel column according to standard procedures. Elute with 10% ethanol, solution (v:v, ethanol:water) at the flow rate of 1 mL/min, collect elute in 30 mL/fraction. Combine fractions with L-α-GPC after HPLC-ELSD analysis. The GPC fraction was decolorized with activated carbon at 80° C. for 1.5 hour, and dried under reduced pressure at 75° C. 9.46 g high purity L-α-GPC was obtained at the end with a final yield of 77.8%.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A method for preparing L-alpha glycerylphosphorylcholine (L-α-GPC) comprising steps of:
   (a). hydrolyzing a phospholipid solution containing phosphatidylcholine by use of phospholipase $A_1$ to remove fatty acids at both the 1- and 2- position of phosphatidylcholine, in the presence of calcium salt ($CaX_n$) to prepare a GPC mixture;
   (b). using a silica gel column chromatography to separate L-α-GPC from said GPC mixture.

2. The method of claim 1 further comprising: using ion-exchange resins to remove cation and anion ions from said GPC mixture.

3. The method of claim 1, wherein the step (a) of the method comprises:
   i. adding said phospholipids in deionized water at a solid-liquid ratio of 1:10-1:30 g/mL;
   ii. adding 2-10% ($CaX_n$(g): phospholipids (g)) calcium salt ($CaX_n$) and 190 U-950 U phospholipase $A_1$/phospholipids (g);
   iii. incubating at 30-60° C. for 3-6 hours.

4. The method of claim 2, comprising:
   i. using a cation-exchange resin to remove cations from said GPC mixture;
   ii. using an anion-exchange resin to remove anions from said GPC mixture.

5. The method of claim 1, further comprising decolorizing the L-alpha glycerylphosphorylcholine with a decolorant.

6. The method of claim 5, wherein said decolorant is activated carbon or attapulgite.

7. The method of claim 1, wherein the step (b) of the method comprises:
   i. adding silica gel to a low carbon chain alcohol;
   ii. adding said GPC mixture to said silica gel;
   iii. eluting with 0-100% a low carbon chain alcohol solution (v:v, alcohol:water);
   iv. collecting fractions at 10-60 mL/fraction.

8. The method of claim 1, wherein said phospholipid is food-grade Lecithin powder.

9. The method of claim 1, wherein said calcium salt is $CaCl_2$, $CaBr_2$, or $CaI_2$.

10. The method of claim 2, wherein said cation-exchange resin is a hydrogen form of a strong acid cation exchange resin, a weak acid cation exchange resin, or a macroporous type cation exchange resin; wherein said anion exchange resin is a hydroxide form of a strong base anion exchange resin, a weak base anion exchange resin, or a macroporous type anion exchange resin.

11. The method of claim 1, wherein the weight of said silica gel ranges from 20 to 100 times of the weight of said GPC mixture.

12. The method of claim 7, wherein collection volumes are based on the weight of said GPC mixture, ranging from 1:1-1:50 (weight of said GPC mixture (g): collection volume (mL)).

13. The method of claim 7, wherein said low carbon chain alcohol is methanol or ethanol.

14. The method of claim 3, wherein said calcium salt is $CaCl_2$, $CaBr_2$, or $CaI_2$.

* * * * *